United States Patent [19]

Goetz

[11] 4,059,640

[45] Nov. 22, 1977

[54] TRANSALKYLATION OF TERTIARY AMINES AND ALCOHOLS, TO PRODUCE ETHYLENE GLYCOL

[75] Inventor: Richard W. Goetz, Cincinnati, Ohio

[73] Assignee: National Distillers and Chemical Corporation, New York, N.Y.

[21] Appl. No.: 625,801

[22] Filed: Oct. 28, 1975

[51] Int. Cl.$^2$ ............................................. C07C 29/00
[52] U.S. Cl. ........................... 260/635 R; 260/583 P; 260/635 D; 260/583 R
[58] Field of Search .......... 260/583 R, 635 R, 635 D, 260/583 P

[56] References Cited

U.S. PATENT DOCUMENTS

| | | | |
|---|---|---|---|
| 2,108,147 | 2/1938 | Speer | 260/583 R |
| 2,390,766 | 12/1945 | Zellhoefer et al. | 260/583 P |
| 2,750,417 | 6/1956 | Closson et al. | 260/583 R X |
| 3,201,471 | 8/1965 | Fisher et al. | 260/583 P |
| 3,732,311 | 5/1973 | Baron | 260/583 P X |
| 3,767,709 | 10/1973 | Fenton | 260/583 R |
| 3,922,303 | 11/1975 | Takehara et al. | 260/583 R X |

*Primary Examiner*—Allen B. Curtis
*Attorney, Agent, or Firm*—Kenneth D. Tremain

[57] ABSTRACT

A tertiary amine and an alcohol are transalkylated. The tertiary amine is reacted with the alcohol, or with the formate ester of the alochol, at a temperature of from about 50° to 300° C. When the reaction is effected using the alcohol (rather than its formate ester), then the reaction is carried out in the presence of carbon monoxide.

6 Claims, No Drawings

TRANSALKYLATION OF TERTIARY AMINES AND ALCOHOLS, TO PRODUCE ETHYLENE GLYCOL

BACKGROUND OF THE INVENTION

1. Field of the Invention

This invention relates to a method of transalkylating a tertiary amine and an alcohol. The tertiary amine is reacted with the alcohol or with the formate ester thereof, without the need of having a metal catalyst present. The transalkylation reaction of the present invention provides an effective method for preparing desired tertiary amines, desired alcohols, or both.

2. Description of the Prior Art

The reaction of a tertiary amine with an alcohol to effect transalkylation is known. Heretofore, however, it was thought necessary to catalyze this reaction with a metal or metal oxide catalyst, such as Co, Ni, Fe, Ru, or copper chromite modified with $MnO_2$ or BaO. See, e.g., Takehara et al, Vol. 19 Yakagaku 957-62 (1970). See also U.S. Pat. No. 3,767,709 (Ru, Os, Rh, Tc).

The carbonylation of alcohols to form their formate esters is known to take place in the presence of alkaline compounds, namely alkali and alkaline earth metal compound catalysts. See U.S. Pat. No. 3,816,513. The formation of quaternary ammonium carboxylates from methyl esters and tertiary amines has also been described. See Kametani et al, J. Heterocyclic Chemistry, Vol. 3, 129–136 (1966). Further, the thermal decomposition of quaternary ammonium carboxylates to give carboxylate esters has been described. See Smith, "Open-Chain Nitrogen Compounds", Vol. 1, 57-58, and Wilson et al, Tetrahedron, Vol. 24, 5493-97 (1968).

SUMMARY OF THE INVENTION

It has been found in accordance with the present invention that a tertiary amine and an alcohol can abe transalkylated by reacting the tertiary amine with the alcohol, or with its formate ester, without any metal catalyst or metal compound catalyst being present. The tertiary amine is reacted with an alcohol in the presence of carbon monoxide. Alternatively, the tertiary amine is reacted with the formate ester of the alcohol, in which case carbon monoxide need not be present. The reaction is carried out at a temperature of from about 50° to 300° C.

By appropriate selection of the reactants, desired tertiary amines and/or alcohols can readily be prepared. According to one preferred aspect of the invention, ethylene glycol is prepared, as by reaction of N,N,N',N'-tetramethylethylenediamine with methanol in the presence of carbon monoxide, or alternatively, with methyl formate.

DESCRIPTION OF THE PREFERRED EMBODIMENTS

The transalkylation of a tertiary amine with an alcohol or with the formate ester thereof is a useful method for the preparation of either a desired tertiary amine or a desired alcohol or both. The reaction with an alcohol may be described by the following general equation:

$$R_1R_2R_3N + ROH \rightarrow RR_1R_2N + R_3OH \qquad (1)$$

(R, $R_1$, $R_2$ and $R_3$ are defined hereinafter.)

Although the precise reaction mechanism through which the transalkylation reaction occurs is not known with certainty, it is believed that the reaction proceeds via the intermediate formation of a quaternary ammonium formate. The proposed reaction pathway is shown in the equations below.

$$ROH + CO \xrightarrow{(R_1)_3N} HCOR \qquad (2)$$

$$(R_1)_3N + HCOR \longrightarrow (R_1)_3NR \cdot \overset{\ominus}{OCH} \qquad (3)$$

$$\overset{\oplus}{(R_1)_3NR} \cdot \overset{\ominus}{OCH} \longrightarrow (R_1)_2NR + R_1OH + CO \qquad (4)$$

Thus, the net reaction is:

$$(R_1)_3N + ROH \xrightarrow{CO} (R_1)_2NR + R_1OH \qquad (5)$$

As previously pointed out, the carbonylation of an alcohol to form the corresponding formate ester (equation 2) is known to take place in the presence of alkaline metal compounds. However, the use of an amine as the catalyst is not known. As also pointed out, the formation of quaternary ammonium carboxylates from methyl esters and tertiary amines has been described. However, formate esters (equation 3) have not been so employed. As further noted, the thermal decomposition of quaternary ammonium carboxylates to give carboxylate esters has been described. However, the decomposition of quaternary ammonium formates (equation 4) has not been reported. The overall reaction (equation 5) has not been carried out in the absence of a metal compound catalyst, nor has it been carried out in the presence of carbon monoxide.

As regards the tertiary amine reactant, $R_1R_2R_3N$, each of $R_1$, $R_2$ and $R_3$ may vary widely. One class of tertiary amines which is suitable is that wherein each of $R_1$, $R_2$ and $R_3$ may be a monovalent hydrocarbon radical which may or may not be substituted. Examples of unsubstituted tertiary amines include trialkyl amines having 1 to 10 carbons in the alkyl groups thereof, e.g., trimethylamine, triethylamine, butylethylmethylamine, and the like; aralkyl amines such as dimethylaniline, etc.

When one or more of $R_1$, $R_2$ and $R_3$ is substituted, the substituent may be phenyl, hydroxy, alkoxy, desirably containing from 1 to 10 carbon atoms, or alkanoyl, desirably containing from 1 to 10 carbon atoms. Examples of suitable tertiary amines where one or more of $R_1$, $R_2$ and $R_3$ is substituted include benzyldiethylamine, $$CH_3)_2NC_2H_4OH, \ (C_2H_5)_2NC_3H_6OCH_3,$$
$$(C_2H_5)_2N-(CH_2)_6-\overset{O}{\overset{\|}{O}}CCH_3,$$

and the like.

Another class of suitable tertiary amines are those of the formula:

$$\begin{array}{c} R_1 \diagdown \quad \diagup R_5 \\ NR_4N \\ R_2 \diagup \quad \diagdown R_6 \end{array}$$

wherein $R_1$ and $R_2$ are as previously defined, wherein $R_4$ is a bivalent organic radical, and wherein $R_5$ and $R_6$ have the same definition as $R_1$ and $R_2$. Examples of suitable tertiary amines falling within such class are: N,N,N',N'-tetramethylethylenediamine($R_1=R_2=R_5=R_6=CH_3-$; $R_4=-CH_2-CH_2-$); N,N,N',N'-tetraethylhexamethylenediamine [$R_1=R_2=R_5=R_6=C_2H_5-$; $R_4=-(CH_2)_6-$]; $(CH_3)_2NC_2H_4N(C_2H_5)_2(R_1=R_2=CH_3-$; $R_5=R_6=C_2H_5-$; $R_4=-C_2H_4OC_2H_4-$); N,N,N',N'-tetramethyl-p-phenylenediamine ($R_1=R_2=R_5=R_6=CH_3-$ ; $R_4=-\text{[phenylene]}-$);

a polymeric compound such as $(CH_3)_2NC_2H_4NC_2H_4NC_2H_4N(CH_3)_2(R_1=R_2=R_5=R_6=CH_3-$; with CH$_3$ substituents
$R_4=-C_2H_4-N(CH_3)-C_2H_4-N(CH_3)-C_2H_4-$;
N,N,N',N'-tetraethyl-1,2-diaminocyclohexane { $R_1=R_2=R_5=R_6=C_2H_5-$; $R_4=$ [cyclohexane-1,2-diyl] } ; etc.

As further discussed hereinafter, N,N,N',N'-tetramethylethylenediamine is particularly suitable for use in the production of ethylene glycol, by reaction with methanol or its formate ester. Of course, other N,N,N',N'-tetrasubstituted ethylenediamines are also suitable, i.e., wherein the substituents $R_1$, $R_2$, $R_5$ and $R_6$ are as previously defined.

Yet another class of suitable tertiary amines are heterocyclic amines such as:

N-methylpiperidine

N-methylpyrrolidine

Triethylenediamine 1,4-dimethylpiperazine

N-methylethylene imine

N-ethylmorpholine

N-methyl-N'-(2-hydroxyethyl)piperazine

Strychnine

Morphine and the like.

As discussed hereinafter, a heterocyclic amine that is highly suitable for the production of ethylene glycol (by reaction with methanol or with its formate ester), is triethylenediamine.

The alcohol reactant may be an alkyl, cycloalkyl, arylakyl or arylcycloalkyl alcohol. Examples of suitable alcohols include methanol, ethanol, isopropanol, octanol, cyclohexanol, methylcyclohexanol, 2-ethylhexanol, benzyl alcohol, 2-phenylethanol, benzhydrol, phenylcyclopentanol, and the like. In general, the alcohol should contain from 1 to 15 carbon atoms, and preferably from 1–7 carbon atoms. The most preferred alcohols are methyl alcohol and benzyl alcohol.

The transalkylation reaction is carried out at a temperature of from about 50° to 300° C. A preferred temperature range is from 100° to 225° C.

Of course, carbon monoxide must be present so as to react with the alcohol to form the formate ester thereof. The carbon monoxide partial pressure should be from about 1 atmosphere up to about 300 atmospheres (gauge). The preferred partial pressure range for the carbon monoxide is from about 5 to 150 atmospheres.

As previously pointed out, the alcohol may also be charged in the form of its formate ester, in which case the addition of carbon monoxide is not required.

If desired, an inert gas such as nitrogen or hydrogen may also be added.

The alcohol and tertiary amine are desirably charged in a molar ratio of from about 10:1 to 1:10. A more preferred ratio is from about 5:1 to 1:5.

If desired, a solvent may also be used. Suitable solvents include, by way of example, N,N-dimethylformamide, N,N-diethylacetamide, nitrobenzene, 1,4-dioxane, tetrahydrofuran, acetonitrile, nitroethane, sulfolane, and water.

The reaction may be run batchwise or in a continuous or semi-continuous manner.

Upon completion of the reaction, the reaction products can be readily separated and recovered by conventional techniques. Thus, depending upon the nature of the starting reactants or the resultant products, distillation and/or crystallization may be employed.

In accordance with a preferred embodiment of my invention, the paricular reactants employed are selected so as to result in the production of ethylene glycol. For example, triethylenediamine and methanol (or its formate ester, methyl formate) may be employed, whereby ethylene glycol is readily produced. (See Example 6 hereinafter.)

Alternatively, any N,N,N',N'-tetrasubstituted ethylenediamine, wherein the substituents $R_1, R_2, R_5$ and $R_6$ are as previously defined, may also be reacted with methanol or with methyl formate so as to produce ethylene glycol. This is illustrated in Example 7, wherein N,N,N',N'-tetramethylethylenediamine was utilized.

In the following table, various transalkylation reactions that have been run are set out.

| REACTANTS | | PRODUCTS | |
|---|---|---|---|
| Amine | Alcohol | Amine | Alcohol |
| $(C_2H_5)_3N$ | $CH_3OH$ | $(C_2H_5)_2CH_3N$ + sm. amts. $(CH_3)_2C_2H_5N$ and $(CH_3)_3N$ | $C_2H_5OH$ |
| $(C_2H_5)_3N$ | $CH_3OH$ (a) | Starting materials | |
| $(CH_3)_3N$ | $\phi CH_2OH$ | $\phi CH_2(CH_3)_2N$ | $CH_3OH$ |
| $N(C_2H_4)_3N$ | $CH_3OH$ |  + 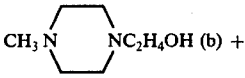 + $(CH_3)_3N$ | $HOC_2H_4OH$ + 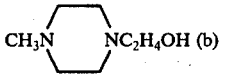 |
| $(CH_3)_2NC_2H_4N(CH_3)_2$ | $CH_3OH$ | $(CH_3)_3N$ + $(CH_3)_2NC_2H_4OH$ (b) | $HOC_2H_4OH$ + $(CH_3)_2NC_2H_4OH$ (b) |

(a) Control run - no carbon monoxide employed.
(b) Aminoalcohol shown in both product columns.

The following examples will further illustrate my invention. All parts are by weight unless otherwise indicated. In all of these examples, the resultant products were identified by gas-liquid chromotography and mass spetroscopy.

EXAMPLE 1

To a glass-lines, stainless steel microreactor were charged 2 ml of methanol, 1 ml of triethylamine, hydrogen (300 psi) and carbon monoxide (500 psi). The reactor was shaken 10 hours at 200° C. The major products, identified by gas liquid chromotography and mass spectrometry, were methyldiethylamine, ethyldimethylamine, trimethylamine and ethanol.

EXAMPLE 2

To a glass-lines, stainless steel microreactor were charged 2 ml of methyl formate, 1 ml of triethylamine, and nitrogen (500 psi). The reactor was shaken 10 hours at 200° C. The products were the same as described in Example 1.

EXAMPLE 3 (Control)

This example was similar to Example 1, except that nitrogen (500 psi) was utilized in lieu of the hydrogen and carbon monoxide employed in Example 1. Only the starting materials were obtained at the conclusion of the experiment.

EXAMPLE 4

To a glass-lined, stainless steel microreactor were charged 2 ml of benzyl alcohol, 1 ml of trimethylamine, and carbon monoxide (900 psi). The reactor was shaken 5 hours at 200° C. A large yield of benzyldimethylamine was obtained.

EXAMPLE 5

To a 35 ml stainless steel reactor were charged 2 gms of triethylenediamine, 10 ml of methyl formate, and carbon monoxide (1000 psi). The reactor was shaken 5 hours at 100° C. The only volatile product, which was present in substantial amounts, was N-methyl-N'-(2-hydroxyethyl)piperazine.

EXAMPLE 6

To a 35 ml stainless steel reactor were charged 2 gms of triethylenediamine, 10 ml of methyl formate, and carbon monoxide (1500 psi). The reactor was shaken 5 hours at 200° C. The conversion of triethylenediamine was complete and the major products, in good yields, were ethylene glycol and methyl cellosolve.

EXAMPLE 7

To a glass-lined, stainless steel 71 ml pressure vessel were charged 5 ml of N,N,N',N'-tetramethylethylenediamine, 10 ml of methanol, and carbon monoxide (650 psi). The reactor was shaken 5 hours at 225° C to give a 34% yield of ethylene glycol and trimethylamine.

EXAMPLE 8 (Control)

To a glass-lined, stainless steel 71 ml pressure vessel were charged 5 ml of N,N,N',N'-tetramethylethylenediamine and 10 ml of methanol, followed by heating with agitation for 5 hours at 200° C. No reaction occurred, with only the starting reactants being recovered.

EXAMPLE 9

To a glass-lined, stainless steel 71 ml pressure vessel were charged 5 ml of N,N,N',N'-tetramethylethylenediamine, 4 ml of methanol, 10 ml of dimethylformamide, and carbon monoxide (700 psi). The vessel was shaken 5 hours at 200° C. A 42% yield of 2-(dimethylamino) ethanol was obtained.

Variations can, of course, be made without departing from the spirit and scope of the invention. Accordingly, it is intended that the preceding description should be construed as illustrative and not in a limiting sense.

I claim:

1. A method of producing ethylene glycol comprising reacting at a temperature of from about 50° to 300° C. a tertiary amine with an alkyl, cycloakyl, aralkyl or acylcycloalkyl alcohol containing up to 10 carbon atoms in the presence of carbon monoxide or with the formate ester of said alcohol, said tertiary amine being triethylenediamine or an amine of the formula

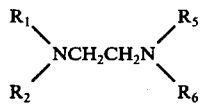

wherein each of $R_1$, $R_2$, $R_5$ and $R_6$ is an acylcic aliphatic hydrocarbon radical of up to 10 carbon atoms or a substituted acyclic aliphatic hydrocarbon radical wherein the substituent is hydroxy, alkoxy of up to 10 carbon atoms or alkanoyl of up to 10 carbon atoms.

2. The method of claim 1 wherein triethylenediamine and methanol are utilized as the reactants, said reaction being carried out in the presence of carbon monoxide.

3. The method of claim 1 wherein triethylenediamine and methyl formate are utilized as the reactants.

4. The method of claim 1 wherein N,N,N',N'-tetramethylethylenediamine and methanol are utilized as the reactants, said reaction being carried out in the presence of carbon monoxide.

5. The method of claim 1 wherein N,N,N',N'-tetramethylethylenediamine and methyl formate are utilized as reactants.

6. A method for producing ethylene glycol comprising reacting methanol and triethylenediamine at a molar ratio of 10:1 to 1:10 in an anclosed reaction zone at a temperature of 50° to 300° C in the presence of carbon monoxide suppplied at a partial pressure of 1 to 300 atmospheres.

* * * * *